United States Patent [19]

Herczog

[11] 4,232,676

[45] Nov. 11, 1980

[54] SURGICAL CUTTING INSTRUMENT

[75] Inventor: Andrew Herczog, Hammondsport, N.Y.

[73] Assignee: Corning Glass Works, Corning, N.Y.

[21] Appl. No.: 961,192

[22] Filed: Nov. 16, 1978

[51] Int. Cl.³ .............................................. A61B 17/39
[52] U.S. Cl. ........................... 128/303.14; 128/303.17
[58] Field of Search ........... 128/303.1, 303.13, 303.14, 128/303.17, 303.18, 783, 784, 799, 800, 804

[56] References Cited

U.S. PATENT DOCUMENTS

| Re. 29,088 | 12/1976 | Shaw | 128/303.17 |
|---|---|---|---|
| 3,970,088 | 7/1976 | Morrison | 128/303.14 |
| 3,987,795 | 10/1976 | Morrison | 128/303.14 |
| 4,033,351 | 7/1977 | Hetzel | 128/303.14 |
| 4,043,342 | 8/1977 | Morrison, Jr. | 128/303.14 |
| 4,161,950 | 7/1979 | Doss et al. | 128/303.14 |

FOREIGN PATENT DOCUMENTS

| 2303515 | 10/1976 | France | 128/303.14 |
|---|---|---|---|
| 2303517 | 10/1976 | France | 128/303.14 |

*Primary Examiner*—Lee S. Cohen

*Attorney, Agent, or Firm*—John P. DeLuca; Burton R. Turner

[57] ABSTRACT

The present invention provides a surgical cutting instrument having a blade portion and cutting edge therefor with electric input elements located near the cutting edge for cutting the tissue and cauterizing the surfaces of the incision, thereby allowing surgery to be more rapidly performed. This is accomplished in accordance with the illustrated embodiments of this invention by providing electrodes of opposed polarity, applied to the blade, near the cutting edge. With an electrical potential applied, no current will flow between the electrodes and no heat is produced unless the electrode gap is bridged by a conducting medium such as a high conductivity physiological fluid. Heat is then generated by electric discharge below an arcing threshold in all areas where the blade is in contact with moist tissue. Little electric discharge or heat occurs elsewhere. Moreover, if movement of the blade is halted, heat generation will substantially diminish as the cut tissue becomes dry as a result of cauterization. A process according to the present invention may include hemostasis of intact tissue and selected use of the instrument for cutting other materials compatible with the process.

7 Claims, 5 Drawing Figures

SURGICAL CUTTING INSTRUMENT

BACKGROUND OF THE INVENTION

During application of a surgical knife or scalpel bleeding can be reduced by cauterizing the cut tissue through heat. According to the prior art, this can be obtained, for example, by applying resistance elements near the cutting edge of the scalpel which is electrically heated to provide a temperature of 200°-500° C. in contact with the tissue. In doing so, however, parts of the blade not in contact with tissue may become grossly overheated, presenting a hazard to both patient and surgeon. Several methods have been recommended to overcome this problem. Generally, all have disadvantages. For example, segmented heating elements require individual temperature-power control systems; heating elements with a large negative temperature coefficient of resistance (TCR) require a very high voltage drive; and, high frequency electric discharge applied through the patient's body produces bad scars and is hard to control.

SUMMARY OF THE INVENTION

Accordingly, the present invention provides a surgical cutting instrument having a blade portion and cutting edge therefor which is adapted with electric input elements for cutting the tissue and cauterizing the surfaces of the incision, thereby allowing surgery to be more rapidly performed. This is accomplished in accordance with the illustrated embodiments of this invention by applying electrodes of opposed polarity to the blade near the cutting edge. With an electrical potential applied, no current will flow between the electrodes and no heat is produced unless the electrode gap is bridged by a conducting medium, such as moist tissue rendered conductive by the presence of physiological fluid. Heat is then generated by electric discharge below an arcing threshold in all areas where the blade is in contact with moist tissue. No electric discharge or heat occurs elsewhere. Moreover, if movement of the blade is halted, heat generation will automatically diminish as the tissue becomes dry as a result of cauterization. Cauterization and hemostasis may occur in both intact and incised tissue.

The electrodes may be made of films of platinum, palladium and other stable metals or alloys satisfying physiological requirements. While the potential applied may be DC or AC, the latter is preferred. In AC mode of operation, particularly at higher frequencies, the system will react as a lossy capacitor when a high conductivity material such as salt-containing water appears within the electrode gap or fringing field between electrode segments. In this case, the heating effect can be controlled by frequency modulation.

The substrate or blade is formed of an insulating material, preferably a glass or glass-ceramic or ceramic with fine grains. The present invention may take various forms for example:
(a) a substrate either conductive or non-conductive having interleaved alternate layers of conductors and insulators near the cutting edge to produce heating by conduction or discharge through the moist incised tissue;
(b) sets of longitudinal electrodes applied to one or both sides of blade having interleaved conductive fingers;
(c) a metallic cutting edge providing a common connection to one electrode on both sides of the blade; or
(d) one electrode connected on each side of blade, interleafing across the cutting edge.

Herczog and Murphy describe (a) and (c) in their U.S. application Ser. No. 961,189 filed this same date and assigned to Corning Glass Works, the assignee herein.

The handle of the cutting instrument is electrically insulated from the blade. To permit comfortable use of the instrument, the handle and blade are lightweight detachable modules for easy replacement and interchangeability with blades having cutting edges of various shapes and sizes determined by the nature of the incision to be made and the tissue to be cut.

DESCRIPTION OF THE PREFERRED EMBODIMENT

Figure 1A:
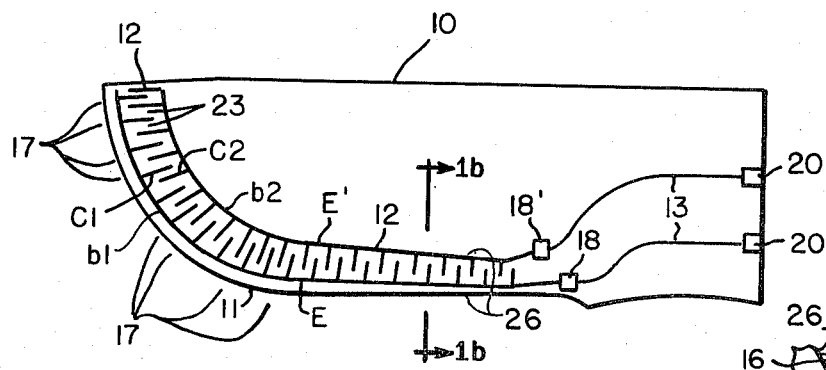
FIG. 1a is a schematic side view of an embodiment of the present invention.

In FIG. 1a there is shown in schematic from a preferred embodiment of the present invention illustrating the basic principle of operation. A substrate of an insulating material forms a surgical instrument or blade 10 having a cutting edge portion 11. The blade 10 carries electric input elements 12 which are conductive and are labeled respectively as electrodes E and E'. The input elements 12 may be metal foil overlays or coatings having interdigitated discrete elements c1 and c2 for respective electrodes E and E'. Conductors 13 are electrically coupled to input elements 12 via leads or contacts 18 and are supplied with high frequency electrical energy.

The present invention will be further described below mainly with respect to incised tissue but it should be understood that incision is not absolutely necessary for the invention to provide hemostasis. The normally moist tissue of a human may be cauterized by the application of electrical energy in accordance with the principles of the present invention since the moist fluid associated with tissue conducts. Thus successful experiments using various forms of animal tissue have shown that the desired effect of cauterization can occur merely by placing the instrument 10 in contact with moist tissue. As physiological fluid dries the process diminishes to a low level but may continue if the instrument is left in one position. The principle described herein does not therefore require incision, release of fluid and cauterization to produce hemostasis as a multistep process but in reality requires the passage of electrical energy through any available electrolytic medium in or on the tissue surfaces to be cauterized. For purposes of explanation however, the main thrust of the disclosure will refer to the practice of incising and cauterizing tissue simultaneously.

Figure 1B:
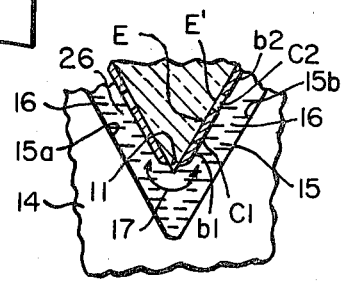
FIG. 1b is a schematic and section view of FIG. 1a taken along line 1b—1b illustrating, the basic principle of operation of the present invention is described including tissue cutting with hemostasis.

In FIG. 1b tissue 14 is incised at 15 by the cutting edge 11 and opposed surfaces 15a–15b of incision 15 has a surface layer of conductive physiological or body fluid 16 exposed. The spacing of blade 10 and surfaces 15a–15b is exaggerated for clarity but in reality they are in intimate contact. The electrical power is conducted to cutting edge 11 via the electric input elements 12 and, physiological fluid 16 provides one or more paths 17 for current conduction from one electrode E to the other E′. A similar process may occur if input elements 12 are also provided for the left side of blade 10. For example, in FIG. 1a the input elements 12 are shown located on one side of the blade 10. However, this arrangement may be duplicated so that each side of the blade has a pair of input elements 12 as illustrated in FIG. 1b described herein. The latter arrangement is preferred.

AC is preferred since undesirable polarization of the electrodes E-E′ and muscular stimulation is possible when DC is used. Further, high frequency AC of 100 kHz–10 mHz is preferred since the input voltage can be as low as 30–50 volts, well below a threshold for arcing.

As the incision 15 is cauterized by the heat generated along conduction paths 17, the body fluid 16 is dried by the heating action. Thus conduction paths 17 disappear and the process is self-limited. As the incision 15 is lengthened or deepened the newly incised portions again release body fluid 16 and the current flows in that newly moistened area. The present invention does not require complex control of portions or segments of the blade 11 since the current paths 17 are produced only when the tissue 14 in incision 15 is moist, i.e. there is body fluid 16 present, resulting from a fresh incision. Wide temperature excursions causing overheating of tissue or portions of the blade 10 is thereby eliminated.

Figure 2:
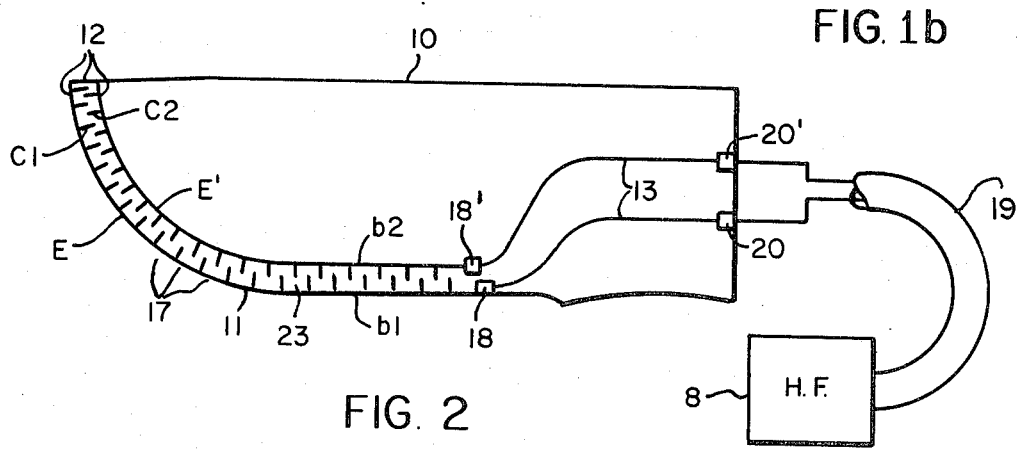
FIGS. 2-3 show variations of the present invention wherein an elongated electrode is located on one or both the sides of a blade with interleaved patterns of conductive fingers.
Figure 3:
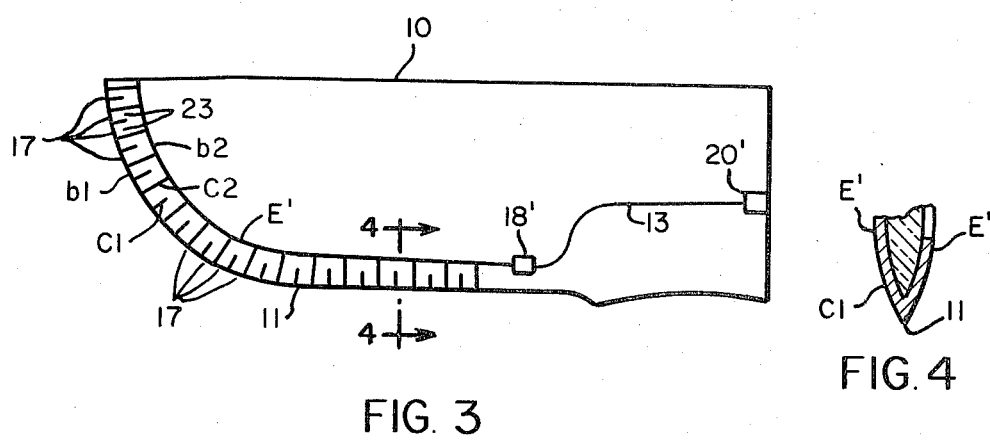

Referring now to FIGS. 2 and 3 of the drawing, there is shown another preferred embodiment of the present invention, wherein similar elements illustrated and explained with regard to FIG. 1 are referenced with the same numerals. The surgical cutting instrument 10 includes the blade cutting edge 11 formed in the desired shape of a surgical cutting instrument which is detachable from handle or holder not shown. The blade 10 may sometimes hereinafter be referred to as a substrate as it carries the electrical input elements 12 thereon disposed in the region of the cutting edge 11. Electrical connections 13 couple input elements 12 to a high frequency voltage source 8 via contacts 18-18′, cable 19 and cable connectors 20-20′. The input elements 12 may be comprised of electrodes E and E′, the former deposited as a layer of conductive film along the cutting edge 11 and having interdigitated fingers c1. The arrangement is similar to FIG. 1 except that the electrode E1 is adjacent and deposited on the cutting edge. The electrode E′ is spaced away from cutting edge 11 and carries fingers c2 which are interdigitated with the fingers c1 of electrode E to provide potential current path sites 17 from electrode E to E′.

As mentioned previously, it is contemplated, in the present invention that the tissue 14 is conductive fluid due to the presence of body fluid 16 bound up in cells (not shown) on the surfaces of intact tissue or surfaces of newly incised tissue, (see FIG. 1). Such fluid satisfactorily conducts electricity. Once the region of the incision 15 is cauterized, the fluid 16 in the vicinity of the incision 15 or area of contact with blade 10 dries and the electrical current reduces by a self-limiting process. This localizes the portion of the input element 12 in which power is dissipated to the portion in contact with moist tissue 14 (see FIG. 1b). The tissue temperature near such portions of the input element 12 may thus be maintained substantially constant.

In the embodiments of the present invention, illustrated in FIGS. 1a–2, heating elements 12 are disposed near the cutting edge 11 on one side of blade 10. The input element 12 is formed with the interdigitated comb-like fingers c1 and c2 projecting from respective electrodes E and E′ towards the opposite one. This interdigitation provides paths 7 for current flow across spaces 23 on the surface of the substrate 10. In FIG. 1a the input element 12 is spaced away from the cutting edge 11 while in FIG. 2 one electrode E of input element 12 is formed as a part of the cutting edge 11 and may be coextensive therewith.

Figure 4:
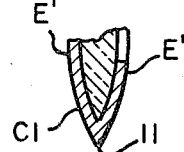
FIG. 4 is a fragmented end section taken along line 4—4 of FIG. 3.

In FIGS. 3 and 4 the electrode E′ with its comblike fingers c2 is deposited on one side (right) of substrate 10 and the fingers c2 extend across cutting edge 11 to the opposite side. Likewise the electrode E is deposited on the opposite side (left) of the blade with portions of its fingers c1 extending across the cutting edge 11 to the side shown. The fingers c1 and c2 form a interdigitated pattern with each other. Current paths 17 are provided laterally along the cutting edge 11 across insulated spaces 23 while the blade 10 is in contact with moist tissue 14 (see FIG. 1b). The current paths 17 of input element 12 are all parallel-connected between the electrodes E and E′.

Contacts 18-18′, leads 13, and cable connectors 20-20′ may be formed of a material such as platinum, gold, tungsten or the like, which makes good contact with the input element 12 material and does not readily oxidize at elevated operating temperatures. The input element 12 may consist of tin oxide or possibly one of the noble metals mentioned above.

In each of these embodiments, the cable connectors 20-20′ are coupled to a suitable high frequency voltage generator 8 (see FIG. 2), which may be a conventional, well-regulated power supply which is capable of delivering the total current required by all portions of input element 12 while maintaining the voltage between electrodes E-E′ substantially constant as various portions conduct. With constant voltage applied to the electrodes, the moist regions draw correspondingly more current and dissipate more power than the dry regions, thereby tending to maintain the tissue in contact with input element 12 all along the cutting edge 11 at a sufficiently high temperature to effect cauterization and hemostasis. The operating temperature at the cutting edge 11 may be controlled by altering the output power and frequency of the high frequency voltage generator 8. Experimental conventional HF generators and power supplies have been used to test the principles of operation of the present invention. To assure substantially uniform operating temperature over the length of the cutting edge 11, the input element 12 should have substantially uniform resistance per unit area, lower than the resistance of the tissue exposed to the input element 12.

Metals for electrodes can be chosen from precious and semiprecious metals mentioned above, as well as stainless steels and others, depending on the intended use.

An important advantage of the use of closely spaced electrodes E-E′ is that the low voltage essentially eliminates arcing typical for most high frequency electrosurgical devices presently known. At low voltages, without arcing, flow of electricity between opposite electrodes is possible only by contact with moist tissue 14 contacting high conductivity physiological fluids 16. With cauterizing, the incised tissue 15 surfaces become dry and the conductive connection between electrodes E-E' ceases because the voltage is not sufficient for arc formation. This feature has the advantages of avoiding tissue burns, self-limiting control of electric power, and constant voltage and power consumption control with respect to cutting rate or variation thereof in the area of the tissue to be incised at any instant in time.

In the preferred embodiment of FIG. 1 each blade 10 shown has a similar end section profile. For purposes of explanation, the arrangement of FIG. 1 will be detailed bearing in mind the other similar arrangements. The substrate or blade 10 may be manufactured from a hard glass, glass-ceramic or ceramic sufficiently fine grained or homogeneous and strong for making a good cutting edge. The thickness of the blade 10 decreases to about 0.15 millimeters near the cutting edge 11. Two strips of appropriately shaped metal foil, or metal coatings b1-b2 are applied to one or both sides of the blade 10 before the cutting edge 11 is formed. In this manner one assures that the electrodes E-E' are placed as close as possible to the cutting edge 11 which is formed by removal of some of the material of the heating element 12. For example Corning Code 1723 glass can be sealed to molybdenum foil by pressing in a vacuum at elevated temperature above the softening point of the glass. Other glasses and ceramics can be used with matched thermal expansion by sealing foils or by other metallizing processes. For very thin metal films (less than 1 millimeter) or films made from ductile metal such as aluminum, silver, platinum, gold, etc., matching thermal expansion is less critical.

For the blade 10 illustrated in FIG. 1 strips of 0.1 millimeter molybdenum metal cover the tapered portion 26 of the substrate 10 near the cutting edge 11. Such a coating of foil also provides for some reinforcement of the substrate 11 in the tapered portion 26. If thin electrically conductive films are used for the input element 12, the glass in the tapered region 26 could be formed thicker for providing more strength. Thin metal films of less than one millimeter are preferably made of tin oxide, platinum or gold or alloys thereof because of their good adherence to the substrate 10 and their electrochemical stability.

It has been mentioned that the operation is self-controlling if the voltage is kept at a certain value below the threshold for arcing. For the device shown in FIG. 1 the voltage may be in the range of about 80 to 20 volts as determined by the spacing between the electrodes E-E' near the cutting edge 11. Any decrease in the spacing of the electrodes E-E' will decrease the required voltage. Power dissipation will vary with the cutting rate and the contact area with the incised tissue at 15, and it is contemplated that the range of power dissipation is between about 5 and about 50 watts. High frequency power is used to minimize nerve stimulation and to avoid electrical polarization of the incision 15 including side reactions. The range of frequencies which has been found useful is between about 10 kilohertz and 10 megahertz. With such a wide frequency range a power supply having a varialbe frequency output can be used as a means of impedance matching the circuit of the power supply with the circuit of the surgical instrument 10 including the input element 12, and the electrical connections coupling power thereto. Generally the power supply setting should be chosen so as to maximize power at the lowest possible voltage for a given blade configuration. In this connection it is preferred that electrode spacing between fingers C1-C2 in FIGS. 1a-3 should be from about 0.1 to about 1 mm to reduce the possibility of arching at the power settings comtemplated.

The present invention is useful for other applications requiring a heated cutting edge, not withstanding the main thrust of the disclosure for a surgical instrument. For example the invention could be used to cut materials which are electrically conductive or rendered conductive by the presence of working fluids and the like, so that cutting and perhaps sealing could simultaneously occur.

While there have been described what are considered to be the preferred embodiments of the present invention it will be obvious to one skilled in the art that various changes and modifications may be made therein without departing from the invention and it is intended in the appended claims to cover all such changes and modifications which fall within the true spirit and scope of the invention.

I claim:

1. A surgical instrument adapted to be coupled to a source of electrical power for cauterizing tissue which is moist and electrically conductive due to the presence of physiological fluid and for simultaneous hemostasis thereof, the instrument comprising:

a blade, a cutting edge formed integrally with said blade along an edge thereof for incising tissue, and at least one pair of electrically-conductive electrodes disposed in the vicinity of the cutting edge in spaced relation to each other and adapted to be electrically coupled to the source of power, each electrode formed as an electrically conductive film surface on the blade surface including a common current carrying member evenly spaced from the cutting edge and integral transverse elongated narrow fingers extending therefrom being relatively closely interdigitated with fingers of another of said electrodes, a distal end of each of said fingers for an electrode being located on the same blade surface as the common current carrying member for the other electrode to conduct electrical power along a plurality of electrical current paths transversely from one finger to an immediately adjacent interdigitated finger for directly heating the tissue along the cutting edge in response to the electrical power applied thereto; and connection means on said instrument providing electrical connections to said electrodes for supplying the electrical power thereto.

2. The surgical cutting instrument of claim 1 wherein said electrodes are disposed in lateral spatial relationship on opposite sides of said cutting edge with a distal portion of each finger traversing said cutting edge.

3. The surgical cutting instrument of claim 1 wherein said electrode spacing is between about 1 and 0.1 millimeters.

4. A method of effecting simultaneous cauterization and resulting hemostasis in tissue comprising the steps of:

contacting the tissue with a tissue cauterizing means;
impressing a voltage from about 20 to about 80 volts across the cauterizing means;
alternating the impressed voltage at a frequency from about 10 KHz to about 10 MHz;

maintaining said impressed voltage below a threshold for arcing establishing an elevated temperature in tissue by conducting current only along a plurality of current paths located along said cauterizing means which are in contact with relatively moist tissue;

dissipating between about 5 to 50 watts of average power in regions of the cauterizing means which are selectively conductive upon contact with moist tissue for the purpose of cauterizing said tissue and thereby producing hemostasis.

5. The method according to claim 4 wherein: conducting of current along the plurality of current paths is dependent on the conductivity of the tissue.

6. The method according to claim 4 wherein dissipating power in the region of the cauterization means in contact with moist tissue results in increasing the resistance of the current paths by decreasing moisture of the tissue.

7. The method according to claim 4 further including the step of: orienting the current paths in at least one of the directions along and across the cauterization means.

* * * * *